US008999408B2

(12) United States Patent
Antony

(10) Patent No.: US 8,999,408 B2
(45) Date of Patent: Apr. 7, 2015

(54) AMLA EXTRACT FOR TRANSDERMAL APPLICATION

(76) Inventor: Benny Antony, Ankamaly (IN)

( * ) Notice: Subject to any disclaimer, the term of this patent is extended or adjusted under 35 U.S.C. 154(b) by 323 days.

(21) Appl. No.: 12/382,602

(22) Filed: Mar. 19, 2009

(65) Prior Publication Data

US 2009/0238780 A1 Sep. 24, 2009

Related U.S. Application Data

(63) Continuation of application No. PCT/IN2006/000380, filed on Sep. 20, 2006.

(51) Int. Cl.
A61K 36/185 (2006.01)
A61Q 19/08 (2006.01)
A61K 8/34 (2006.01)
A61K 8/67 (2006.01)
A61K 8/97 (2006.01)

(52) U.S. Cl.
CPC ............ *A61Q 19/08* (2013.01); *A61K 8/347* (2013.01); *A61K 8/676* (2013.01); *A61K 8/97* (2013.01); *A61K 2800/522* (2013.01)

(58) Field of Classification Search
CPC ....................................................... A61K 8/00
USPC .................................. 424/777, 72, 401, 725
See application file for complete search history.

(56) References Cited

U.S. PATENT DOCUMENTS

| 6,124,268 | A  | * | 9/2000  | Ghosal ........................ 514/27 |
| 6,235,721 | B1 | * | 5/2001  | Ghosal ........................ 514/25 |
| 6,290,996 | B1 |   | 9/2001  | Ghosal |
| 6,362,167 | B1 |   | 3/2002  | Ghosal |
| 6,649,150 | B2 |   | 11/2003 | Chaudhuri |
| 7,001,619 | B2 |   | 2/2006  | Johri et al. |
| 2001/0016213 | A1 | * | 8/2001  | Singh-Verma ............ 424/725 |
| 2003/0008048 | A1 |   | 1/2003  | Winston et al. |
| 2003/0194452 | A1 |   | 10/2003 | Agarwal et al. |
| 2005/0089590 | A1 | * | 4/2005  | Chaudhuri .................. 424/769 |

FOREIGN PATENT DOCUMENTS

| WO | WO 96/24327 A | 8/1996 |
| WO | WO 02/23995 A | 3/2002 |

OTHER PUBLICATIONS

Khopde et al. "Characterizing the antioxidant activity of Amla (*Phyllantus emglica*) extract", Current Science, vol. 81, No. 2, Jul. 25, 2001.*
Ghosal, S, Tripathi, VK and Chauhan S, Active Constituents of*Emblica officinalis*: Part 1-The Chemistry and Antioxidative Effects of Two New Hydrolysable Tannins, Emblicanin A and B, Indian Journal of Chemistry, 35B: 941-948 (1996).
Anila, L, and Vijayalakshmi, NR, Flavonoids from *Emblica officinalis* and *Mangifera indica*—Effectiveness for Dyslipedemia, Journal of Ethnopharmacology, 79: 81-87 (2002).
Brewer, HB, High-Density Lipoproteins: A New Potential Therapeutic Target for the Prevention of Cardiovascular Disease, Arterioscler. Thromb. Vase. BioL, 24: 387-391 (2004).
Brewer, HB, Increasing HDL Cholesterol Levels, N. Engl. J. Med., 350 (15): 1491-1494 (2004), Massachusetts Medical Society.
Furberg, CD, Adams, HP, Applegate, WB, Byington, RP, Espeland, MA, Hartwell, T, Hunninghake, DB, Lefkowitz, DS, Probstfield, J, and Riley, WA, Effect of Lovastatin on Early Carotid Artherosclerosis and Cardiovascular Events. Asymptomatic Carotid Artery Progression Study (ACAPS) Research Group, Circulation, 90: 1679-1687 (1994), American Heart Asociation.
Navab, M, Anantharamaiah, GM, Hama, S, Garber, DW, Chaddha, M, Hough, G, Lallone, R, and Fogelman, A, Oral Administration of an Apo A-1 Mimetic Peptide Synthesized From D-Amino Acids Dramatically Reduces Atherosclerosis in Mice Independent of Plasma Cholesterol,Circulation, 105: 290-292 (2002), American Heart Association.
Grundy, S, Statin Trials and Goals of Cholesterol-Lowering Therapy, Circulation, 97: 1436-1439 (1998), American Heart Association.
Ridker, PM, Clinical Application of C-Reactive Protein for Cardiovascular Disease Detection and Prevention, Circulation, 107: 363-369 (2003), American Heart Association.
Ridker, P, Cannon, CP, Morrow, D, Rifai, N, Rose, LM, McCabe, CH, Pfeffer, MA, and Braunwald, E, C-Reactive Protein Levels and Outcomes after Statin Therapy, N. Engl. J. Med., 352:20-28 (2005), Massachusetts Medical Society.
Chew, DP, Bhatt, DL, Robbins, MA, Penn, MS, Schneider, JP, Lauer, MS, Topol, EJ, and Ellis, SG, Incremental Prognostic Value of Elevated Baseline C-Reactive Protein Among Established Markers of Risk in Percutaneous Coronary Intervention, Circulation, 104: 992-997 (2001), American Heart Association.
Haffner, SM, Lento, S, Ronnemaa, T, Pyorala, K, and Laakso, M, Mortaliy from Coronary Heart Disease in Subjects with Type 2 Diabetes and in Nondiabetic Subjects With and Without Prior Myocardial Infarction, N. Engl. J. Med., 339 (4): 229-234 (1998), Massachusetts, Medical Society.
Malmberg, K, Yusuf, S, Gerstein, HC, Brown, J, Zhao, F, Hunt, D, Piegas, L, Calvin, J, Keltai, M, Budaj, A, and for the OASIS Registry Investigators, Impact of Diabetes on Long-Term Prognosis in Patients with Unstable Angina and Non-Q-Wave Myocardial Infarction: Results of the OASIS (Organization to Assess Strategies for Ischemic Syndromes) Registry, Circulation, 102:1014-1019 (2000), American Heart Association.
Sawin, CT, Geller, A, Wolf, PA, Belanger, AJ, Baker, E, Bachrach, P, Wilson, P, Benjamin, EJ, and D'Agostino RB, Low Serum Thyotropin Concentrations as a Risk Factor for Atrial Fibrillation in Older Persons, N. Engl. J. Med., 331: 1249-1252 (1994).
Klein, I, and Ojamaa, K, Thyroid Hormone and the Cardiovascular System, N. Engl. J. Med., 344(7): 501-509 (2001), Massachusetts Medical Society.

(Continued)

*Primary Examiner* — Chris R Tate
*Assistant Examiner* — Deborah Davis
(74) *Attorney, Agent, or Firm* — Jyoti C Iyer

(57) ABSTRACT

An extract of *Emblica officinalis* (Amla). Transdermal formulation having an extract of *Emblica officinalis* having exhibiting greater migration of Vitamin C across a skin surface as compared to a transdermal formulation having Vitamin C without the extract. Extract of *Emblica officinalis* exhibiting greater migration of $H^+$ ions across a skin surface as compared to a transdermal formulation having Vitamin C alone. A transdermal formulation having an extract of *Emblica officinalis*. Method of preparing an extract of *Emblica officinalis*.

4 Claims, No Drawings

(56) References Cited

OTHER PUBLICATIONS

Pasceri, V, Willerson, JT, and Yeh, ETH, Direct Proinflammatory Effect of GReactive Protein on Human Endothelial Cells, Circulation, 102: 2165-2168 (2000), American Heart Association.

Sacks, FM, Pfeffer, MA, Moye, LA, Rouleau, JL, Rutherford, JD, Cole, TG, Brown, L, Warnica, JW, Arnold, JMO, Wun, C-C, Davis, BR, and Braunwald, E, for the Cholesterol and Recurrent Events Trial Investigators, The Effect of Pravastatin on Coronary Events After Myocardial Infarction in Patients with Average Cholesterol Levels, N. Engl. J. Med., 335(14): 1001-1009 (1996), Massachusetts Medical Society.

Ross, R, Atherosclerosis—An Inflammatory Disease, N. EngL J. Med., 340(2): 115-126 (1999), Massachusetts Medical Society.

Stefanick, ML, Mackey, S, Sheehan, M, Ellsworth, N, Haskell, WL, and Wood, PD, Effects of Diet aand Exercise in Men and Postmenopausal Women with Low Levels of HDL Cholesterol and High Levels of LDL Cholesterol, N. Engl. J. Med., 339(1): 12-20 (1998), Massachusetts Medical Society.

Pederson, TR, Olsson, AG, Faergeman, O, Kjekshus, J, Wedel, H, Berg, K, Wilhelmsen, L, Haghfelt, T, Thorgeirsson, G, Pyorala, K, Miettinen, T,Christophersen, B, Tobert, JA, Musliner, TA, Cook, TJ, for the Scandinavian Simvastatin Survival Study Group, Lipoprotein Changes and Reduction in the Incidence of Major Coronary Heart Disease Events in the Scandinavian Simvastatin Survival Study (4S), Circulation, 97: 1453-1460 (1998), American Heart Association.

Sacks, FM, Moye, LA, Davis, BR, Cole, TG, Rouleau, JL, Nash, DT, Pfeffer, MA, and Braunwald, E, Relationship Between Plasma LDL Concentrations During Treatment With Pravastatin and Recurrent Coronary Events in the Cholesterol and Recurrent Events Trial, Circulation, 97: 1446-1452 (1998), American Heart Association.

Ridker, PM, Rifai, N, Pfeffer, MA, Sacks, F, and Braunwald, E, Long-Term Effects of Pravastatin on Plasma Concentration of C-Reactive Protein, Circulation, 100:230-235 (1999), American Heart Association.

West of Scotland Coronary Prevention Study Group, Influence of Pravastatin and Plasma Lipids on Clinical Events in the West of Scotland Coronary Prevention Study (WOSCOPS), Circulation, 97: 1440-1445 (1998), American Heart Association.

Juonala, M, Viikari, JSA, Laitinen, T, Marniemi, J, Helenius, H, Ronnemaa, T, and Raitakari, OT, Interrelations Between Brachial Endothelial Function and Carotid Intima-Media Thickness in Young Adults: The Cardiovascular Risk in Young Finns Study, Circulation, 110: 2918-2923 (2004), American Heart Association.

Chen, Z, Fukutomi, T, Zago, AC, Ehlers, R, Detmers, PA, Wright, SD, Rogers, C, and Simon, DI, Simvastatin Reduces Neointimal Thickening in Low-Density Lipoprotein Receptor-Deicient Mice Ater Experimental Angioplasty Without Changing Plasma Lipids, Circulation, 106: 20-23 (2002), American Heart Association.

Sheperd, J, Cobbe, SM, Ford, I, Isles, CG, Lorimer, RA, MacFarlane, PW, McKillop, JH, and Packard, CJ, For the West of Scotland Coronary Prevention Study Group, Prevention of Coronary Heart Disease with Pravastatin in Men With Hypercholesterolmia, N. Engl. J. Med., 333(20):1301-1307 (1995), Massachusetts Medical Scoiety.

Thakur, CP, Thakur, B, Singh, S, Sinha, PK, and, Sinha SK, The Ayurvedic medicines Haritaki,Amla and Bahira Reduce Cholesterol-Induced Atherosclerosis in Rabbits, Intl. J. Cardiology, 21: 167-175(1988).

Thakur, CP, and Mandal, K, Effect of *Emblica oficinalis* on Cholesterol-Induced Atherosclerosis in Rabbits, Indian J. Med. Res., 79: 142-146 (1984), Indian Council of Medical Research.

Sai Ram, M, Neetu, D, Deepti, P, Vandana, M, Ilavazhagan, G, Kumar, D, and Selvamurthy, W, Cytoprotective Activity of Amla (*Emblica officinalis*) Against Chromium (VI) Induced Oxidative Injury in Murine Macrophages, Phytother. Res., 17: 430-433 (2003), John Wiley &Sons, Ltd.

Nemmani, KVS, Jena, GB, Dey, CS, Kaul, CL, and, Ramarao, P, Cell Proliferation and Natural Killer Cell Activity by Polyherbal Formulation, Immu-21 in Mice, Indian Journal of Experimental Biology,40: 282-287 (2002).

Panda, S, and Kar, A, Fruit Extract of *Emblica officinalis* Ameliorates, Hyperthyroidism and Hepatic Lipid Peroxidation in Mice, Pharmazie, 58: 753-755 (2003).

Sabu, MC, and Kuttan, R, Anti-diabetic Activity of Medicinal Plants and its Relationship with their Antioxidant Property, J Ethnopharmacology, 81: 155-160 (2002).

Sai Ram, M, Neetu, D, Yogesh, B, Anju, B, Dipti, P, Pauline, T, Sharma, SK, Sarada, SKS, Ilavazhagan, G, Kumar, D, and Selvamurthy, W, Cytoprotective and Immunomodulation Properties of Amla (*Emblica officinalis*) on Lymphocytes: An In-Vitro Study, J Ethnopharmacology, 81:5-10 (2002).

Muruganandam, AV, Kumar, V, and Bhattacharya, SK, Effect of Poly Herbal Formulation, EuMil, on Chronic Stress-Induced Homeostatic Peturbations in Rats, Indian J Experimental Biology, 40:1151-1160(2002).

Babu, PS, and Prince, PSM, Antihyperglycaemic and Antioxidant Effect of Hyponidd, An Ayurvedic Herbomineral Formulation in Streptozotocin-Induced Diabetic Rats, J Pharmacy and Pharmacology, 56:1435-1442(2004).

Duan, W, Yu, Y, and Zhang, L, Antiatherogenic Effects of *Phyllanthus emblica* Associated with Corilagin and its Analogue, Yakugaku Zasshi, 125(7): 587-591 (2005), The Pharmaceutical Society of Japan.

Tariq, M, Hussain, SJ, Asif, M, and Jahan, M, Protective Effect of Fruit Extracts of*Emblica officinalis* (Gaertn.) & *Terminalia belerica* (Roxb.) in Experimental Myocardial Necrosis in Rats, Indian J. exp. Biol., 15(6): 485-486 (1977).

Mishra, M, Pathak, UN, and Khan, AB, *Emblica officinalis* Gaetn and Serum Cholesterol Level in Experimental Rabbits, Br. J. exp. Path., 62: 526-528 (1981).

Mathur, R, Sharma, A, Dixit, VP, and Varma, M, Hypolipidaemic Effect of Fruit Juice of *Emblica oicinalis* in Cholesrterol-Fed Rabbits, J. Ethnopharmacology, 50: 61-68 (1996), Elsevier Science Ireland Ltd.

Kim, HJ, Yokozawa, T, Kim, HY, Tohda,C, Rao, TP, and Juneja, LR, Influence of Amla (*Emblica officinalis* Gaetn.) on Hypercholesterolemia and Lipid Peroxidation in Cholesterol-Fed Rats, J. Nutr. Sci. Vitaminol., 51: 413-418 (2005).

Bhattacharya, A, Muruganandam, AV, Kumar, V, and Bhattacharya, SK, Effect of Poly Herbal Formulation, EuMil, on Neurochemical Perturbations Induced by Chronic Stress, Indian J. Exp. Biol., 40: 1 161-1163 (2002).

Bhattacharya, SK, Bhattacharya, D, and Muruganandam, AV, Effect of*Emblica officinalis* Tannoids on a Rat Model of Tardive Dyskinesia, Indian J. exp. Biol., 38:945-947 (2000).

One page of International Search Repot dated Dec. 1, 2003, from International Appl. No. PCT/IN03/00137.

Seven (7) pages of European Search Repot dated Jun. 18, 2009.

Nalini D and Kapoor R, Effect of Plant Fruits: Indian Gall Nut, Bedda Nut and Gooseberry—On Hypercholesterolemic Rats, Plant Foods for Human Nutrition, 53(4):343-349 (1999).

Reza MS, Khan BR, Islam B, Muhsin AUM, and Quddus R, Effects of *Emblica officinalis* (amlaki) and Vitamin C on Cholesterol Induced Atherosclerosis in Rabbits, Journal of Bangladesh College of Physicians and Surgeons 1994 BD, 12(1):3-7 (1994).

Rader, DJ, High-density Lipoproteins and Atherosclerosis, American Journal of Cardiology, 90(8A), 62i-70i (2002).

Protest Documents filed by Third Party on Jul. 3, 2011, thirteen (13) pages, in U.S. Appl. No. 12/805,191, filed Jul. 16, 2010.

\* cited by examiner

AMLA EXTRACT FOR TRANSDERMAL APPLICATION

RELATED APPLICATIONS

This Application is a Continuation of co-pending PCT Application Ser. No. PCT/IN2006/000380, filed Sep. 20, 2006, which is incorporated in its entirety by reference.

BACKGROUND

The protein collagen in the dermis or the second layer of the skin provides a strong and healthy skin. Vitamin C has a crucial role to play in collagen synthesis. Collagen synthesis is induced and supported by Vitamin C. Vitamin C being highly water soluble, hence, its availability at the site of collagen synthesis is restricted since the parts of the skin are lipophilic and therefore Vitamin C is easily eliminated from the body. During ageing collagen synthesis is retarded resulting in the falling of the strength and support to the skin. This results in wrinkling and sagging of the skin. Hence it is necessary to devise methods for inducing collagen synthesis vigorously by providing adequate concentrations of Vitamin C at the dermis. Any amount of Vitamin C ingested through oral or other conventional routes cannot provide adequate concentrations of Vitamin C at the site of collagen synthesis and it is now well recognized that providing Vitamin C across the skin structure through topical application is the best way to achieve this. However due to the high water solubility of Vitamin C, its transportation across lipophilic skin membranes is also slow.

The presence of radical oxygen converts dihydroxyphenylalanine (DOPA) to DOPA-quinone, which is further converted to melanin. Melanin is dark brown and it further polymerizes to black melanin pigment and these are responsible for the color of brown and black skins. It has been recognized that the best way to prevent formation of these melanin pigments is to inhibit the oxidation of DOPA to DOPA-Quinone and the conversion further of the latter to melanin pigments. Two agents that inhibit melanin pigment formation are Vitamin C and hydrogen ions. Hydrogen ions in the presence of reducing agents like Vitamin C can inhibit this melanin synthesis and also reverse it, resulting in the whitening of skin.

One of the major causes of melanin pigmentation of the skin is exposure to UV light present in the sun's radiation and various artificial lighting methods. There are ways to protect the skin from UV or actinic radiation by providing applications containing molecules that absorb UV light.

Vitamin C like activity is not confined to ascorbic acid. The Vitamin C bioactivity including anti scorbutic activity, promotion of collagen synthesis and various anti oxidant and free radical scavenging properties, arise from the specific chemical structural feature 1-oxo-2-ene-2, 3-diol, which is referred to as aci-reductones or simply reductones. There are many such reductones in nature especially in fruits and one such fruit containing reductones is the Indian gooseberry also known as Amla in India whose scientific nomenclature is *Emblica officinalis* Gaertn.

The constituents of the Indian gooseberry dry extract described by Ghosal in his patent U.S. Pat. No. 6,235,721 as 'CAPROS' is said to contain the following components and the proportion indicated: An antioxidant blend consisting of, by weight:

Emblicanins A and B, that is,
the gallic acid-ellagic acid esters of 2-keto-gluconodelta lactone: 35-55%;
2,3-di-o-galloyl 4,6-S-hexahydroxydiphenoylgluconic acid (Punigluconin): 4-15%;
2,3,4,6,-bishexahydroxydiphenoyl glucose (Pedunculagin): 10 to 20%, and
about 5 to 15% of 3',4',5,7-tetrahydroxy flavone-3-O-rhamnoglucoside (Rutin);
Tannoids of gallic/ellagic acids 10-30%;
Gallic acid 0-5%; and,
Ellagic acid 0-5%.

Chaudhari et al in their U.S. Pat. No. 6,649,150 on skin lightening or whitening compositions have described the need to restrict the presence of flavonoids like rutin which are yellow colored and not desirable in a skin whitening composition based on the same Indian gooseberry extract. Chaudhuri et al describe a method to select geographically or maturity levels of the fruit or by removing by chromatography the undesirable flavonoid pigment to the minimum that is, below 1% or better, 0.1% or more preferably 0.01%. They have also described the flavonoids to have strong UV absorption in the wavelength region of 350 nanometers.

The composition Chaudhuri et al is reported to have the following content:
Emblicanin A: 20-35%;
Emblicanin B 10-20%;
Pedunculagin 15-30%;
Punigluconin 3-12%; and,
Flavonoids less than 1%.

SUMMARY

The disclosed teachings provide a process for the isolation of an extract of the fruits of *Emblica officinalis* by a specific sensitive process, whereby the extract has nearly no artifact, such as, free gallic and free ellagic acid, which result from hydrolysis of galloellagitannins during processing of the fruits of *Emblica officinalis*, or, oxidation and hydrolysis products of the antioxidants. An extract of *Emblica officinalis* is provided which has a superior transdermal rate of delivery of Vitamin C and $H^+$ ions across the outer skin membrane (epidermis) into the dermis (inner skin) when low concentration of the extract is applied to the skin as compared to application of Vitamin C alone to the skin. A transdermal preparation including the extract of the fruits of *Emblica officinalis* highly suitable for the skin's sensitive layers is provided.

In one embodiment, an extract of *Emblica officinalis* fruit is provided, which includes, by weight,
about 35±5% of galloellagitannin;
about 1-9% of Vitamin C; and,
about 5-60% of carbohydrate. Corilagin is about 0.5-5% of the galloellagitannin. Soluble fiber is about 2-25% of the carbohydrate.

In one embodiment, an extract of *Emblica officinalis* fruit is provided, which includes, by weight, about 35-50% polyphenol. Corilagin is about 0.5-5% of the polyphenol.

In one embodiment, a transdermal formulation having an extract of *Emblica officinalis* fruit is provided. The transdermal formulation having the extract exhibits about a 2 fold greater migration of Vitamin C across a skin surface as compared to a transdermal formulation comprising Vitamin C without the extract.

In one embodiment, a transdermal formulation having an extract of *Emblica officinalis* fruit is provided. The transdermal formulation having the extract exhibits about a 2 fold greater migration of $H^+$ ions across a skin surface as compared to a transdermal formulation comprising Vitamin C without the extract.

In one embodiment, a transdermal formulation having an extract of *Emblica officinalis* is provided.

In one embodiment, a dosage form of a transdermal formulation having an extract of *Emblica officinalis* is provided. The dosage form can be a lotion, cream, ointment or gel for application to skin.

In one embodiment, an extract of *Emblica officinalis* is provided, where the extract is prepared by:

pulping a fruit of *Emblica officinalis* in water at room temperature of about 27degree° C. to obtain a pulp;

drying the pulp at a temperature of about 95 -100° C., and, under a vacuum of about 500-600 mm of Hg to obtain the extract of *Emblica officinalis*.

One embodiment provides a method of increasing transfer of Vitamin C across a skin surface by administering an extract of *Emblica officinalis* as compared to administering Vitamin C alone to the skin surface.

One embodiment provides a method of increasing transfer of $H^+$ ions across a skin surface by administering an extract of *Emblica officinalis* as compared to administering Vitamin C alone to the skin surface.

One embodiment provides a method of inhibiting melanin synthesis by administering an extract of *Emblica officinalis*.

One embodiment provides a method of protecting skin from aging by administering an extract of *Emblica officinalis*.

One embodiment provides a method of protecting skin from actinic radiation by administering an extract of *Emblica officinalis*.

One embodiment provides a method of protecting skin from free radical damage by administering an extract of *Emblica officinalis*.

One embodiment provides a method of protecting skin from ozone by administering an extract of *Emblica officinalis*.

One embodiment provides a method of preparing an extract of *Emblica officinalis* by pulping the fruit of *Emblica officinalis* in water at room temperature of about 10° C. to obtain a pulp. The pulp is dried at a temperature of about 60-70° C., and, under a vacuum of less than about 10 torr to obtain the extract of *Emblica officinalis*.

DETAILED DESCRIPTION

We discovered that one of the active fractions of the mature fruits of *Emblica officinalis* (the Indian gooseberry) contains galloellagitannins, corilagin, Vitamin C, carbohydrate and soluble fibre in a proportion that provides it to be eminently suitable for the preparation of suitable cosmetic/pharmaceutical compositions. The extract of *Emblica officinalis* provides for a very rapid transport of the Vitamin C active reductones released from the polyphenol bonding from the epidermis to the dermis. Therefore, the extract is useful for various known skin applications for augmenting or for the regeneration and synthesis of collagen in the dermis, for inhibiting melanin synthesis, for free radical scavenging, and, for a healthy and fairer skin.

The process adopted by us for preparation of the Indian gooseberry extract includes specially mild and effective techniques like chilling the berry and the extracting with water alone or in combination with pharmaceutically acceptable polar solvents like ethanol, isopropanol etc. In one embodiment the extraction is performed with purified water only to avoid introduction of solvent residues in the food supplement/pharmaceutical product. The extraction method is based on a cold extraction procedure and by uses a technologically superior method of concentration, such as, Agitated thin film evaporator (AFTE) and Agitated thin film drier (ATFD) at a low temperature under a vacuum of about 500-600 mm of mercury (Hg), to preserve the identity of the constituents naturally present in the plant.

The composition of the product (extract of *Emblica officinalis*) so obtained contains active hydrolysable tannins as shown by the presence of gallic acid in the dilute sulphuric acid hydrolyzed portion of the product by its HPLC chromatogram. Some embodiments of the extract of *Emblica officinalis* also contain corilagin. Estimation of corilagin was by a HPLC based method. Carbohydrate was detected by a spectrophotometric method. Soluble fibre was analyzed through gravimetric method. Vitamin C and reductones having Vitamin C like moiety were detected by a titration method using dichloroindophenol. Vitamin C in the extract of *Emblica officinalis* was also qualitatively detected by HPTLC method.

Thus the undesirable rutin and any other flavonoid product as described in patent U.S. Pat. No. 6,649,150 which emphasizes the lower content of flavonoids like rutin to be less than 0.1% as advantageous are excluded from the extract. We have achieved this by the cold and mild extraction and concentration and drying procedure employing state of the art technology, namely use of ATFE and ATFD for processing, thereby extracting mostly the active tannins, namely the gallo-ellagic tannins along with one more hydrolysable tannins.

Studies showed that one embodiment of the extract of *Emblica officinalis* had the following composition:

Galloellagic tannins: 35.5%;

Vitamin C (or reductone; or free Vitamin C and/or Vitamin C like molecules, or derivatives of Vitamin C): 8%;

Corilagin: 0.75%;

Carbohydrate: 29%;

Soluble fibre: 24.55%;

Ellagic acid: 1%; and,

Gallic acid: 1.2%.

One embodiment of the extract of *Emblica officinalis* has the following composition:

Galloellagic tannins: 35±5%;

Vitamin C (which includes reductones; or free Vitamin C and/or Vitamin C like molecules, or derivatives of Vitamin C): 1-9%;

Carbohydrate 5-35%; and,

Soluble fiber: 2 -25%, and, wherein about 0.5-5% of the galloellagitannin is comprised of corilagin.

One embodiment of the *Emblica officinalis* extract has the composition as below:

Galloellagic tannins: 35±5%;

Vitamin C (which includes reductones; or free Vitamin C and/or Vitamin C like molecules) upto 1-9%; and, Carbohydrate—5-60%;

wherein about 0.5-5% of the galloellagitannin is comprised of corilagin, and, wherein about 2-25% of the carbohydrate is comprised of soluble fiber.

In one embodiment, the extract of *Emblica officinalis* includes:

about 35% of galloellagic tannins;

about 7% -9% of Vitamin C;

about 2% free ellagic acid; and, about 2% free gallic acid.

In one embodiment, the extract of *Emblica officinalis* includes:

about 35-50% of polyphenol. Corilagin is about 0.5-5% of the polyphenol.

In some embodiments, it was found that the extract of *Emblica officinalis* after dilute sulphuric acid (10%) hydrolysis gave gallic acid as the sole or most dominant product.

Some embodiments of the extract of *Emblica officinalis* include ellagic acid in almost equal amount to gallic acid. Some embodiments of the extract contain ellagi tannins coming as a single peak along with substantial (ca. 10%) Vitamin C and other gallo-tannins.

One embodiment provides an extract of *Emblica officinalis*, prepared by pulping mature fruits of *Emblica officinalis* in water at room temperature of about 27° C. to obtain a pulp, then, drying the pulp at a temperature of about 95-100° C., and, under a vacuum of about 500-600 mm of mercury to obtain the extract of *Emblica officinalis*.

In one embodiment, analysis of the extract of *Emblica officinalis* by titration with 2,6-dichloroindophenol gave a value of about 7 to about 9% of Vitamin C. HPTLC profile of the extract of *Emblica officinalis* confirmed the presence of Vitamin C in the extract. Since, firstly, the quantitation of Vitamin C was performed using the dichloroindophenol method, which detects the active moiety of Vitamin C, namely the reductone; and, secondly, the reductone moiety might be present in molecules other than in free Vitamin C in the extract of *Emblica officinalis*, such as, in derivatives of Vitamin C, wherein the Vitamin C is not free but attached to, e.g., galloellagic tannins, therefore, the estimated Vitamin C content in embodiments of the extract as provided includes reductones, or reductone equivalent which may include free Vitamin C and/or Vitamin C like molecules.

In some embodiments of the extract of *Emblica officinalis*, the ellagic acid content is about the same percent as gallic acid in the hydrolysate of the extract. HPTLC analysis was used to detect gallic acid qualitatively and quantitatively in the dry extract of *Emblica officinalis*. Ellagic acid was detected by HPLC. In some embodiments of the extract, free ellagic and/or free gallic acid are not found. The lack of free ellagic and free gallic acid, which are usually artifacts of the extraction process, showed that the disclosed process is a mild process that protects the active components of *Emblica officinalis*, such as galloellagitannins, from hydrolysis during the extraction.

Polyphenols include tannins, including galloellagitannin. Other components of polyphenols may include flavonoids and anthocyanins. All tannins including galloellagic tannins are polyphenols. However, not all polyphenols are tannins.

Galloellagitannins are glucose derivatives of gallic and ellagic acid. Corilagin is a galloellagitannin. Corilagin is also a hydrolysable galloellagi tannin. Corilagin content of the extract of *Emblica officinalis* can be determined by high performance liquid chromatography (HPLC) method.

Tannins include hydrolysable and non-hydrolysable tannins. Non-hydrolysable tannins are also referred to as condensed tannins. Hydrolysable tannins include glucose derivatives of gallic and ellagic acid, which are water soluble. Hydrolysable tannin content of the extract of *Emblica officinalis* can be determined by:
(1) Hydrolyzing the dry extract of *Emblica offinalis* with agents such as hydrochloric acid, and estimating the released ellagic acid by methods such as HPLC, and estimating the released gallic acid by methods such as HPTLC. This step yields the total ellagic and gallic acid content of the dry extract of *Emblica officinalis*. (2) Estimating the amount of ellagic acid and garlic acid in the untreated dry extract of *Emblica officinalis*. The content of ellagic acid and gallic acid obtained from the untreated dry extract of *Emblica officinalis* is the free gallic and ellagic acid content of the dry extract of *Emblica officinalis*. (3) The hydrolysable gallic and ellagic acid content of the dry extract of *Emblica officinalis* is obtained by subtracting the value of the free gallic and ellagic acid obtained in step (2) from the total gallic and ellagic acid content as obtained in step (1).

Carbohydrate includes soluble fiber and insoluble components. Insoluble components include insoluble fiber and starch. Carbohydrate content of the dry extract of *Emblica officinalis* can be determined by spectrophotometric method using anthrone reagent. Soluble fiber content of the extract of *Emblica officinalis* can be determined by gravimetric method.

Fiber is largely a carbohydrate. The building blocks of all carbohydrates are different types of sugars and they can be classified according to how many sugar molecules are combined in the carbohydrate. Simple sugars consist of 1-2 sugar molecules such as glucose, fructose, sucrose, maltose, lactose. Oligosaccharides consist of 3-10 glucose molecules joined together. Starch polysaccharides have more than 10 glucose molecules joined together. Non-starch polysaccharides have more than 10 sugar molecules such as xylose, arabinose, and mannose. Dietary fibre includes non-starch polysaccharides, oligosaccharides, liginin (not a carbohydrate) and associated plant substances.

Soluble fiber is "soluble" in water. When mixed with water it forms a gel-like substance and swells. Soluble fiber has many benefits, including moderating blood glucose levels and lowering cholesterol. The scientific names for soluble fibers include pectins, gums, mucilages, and some hemicelluloses. Good sources of soluble fiber include oats and oatmeal, legumes (peas, beans, lentils), barley, fruits and vegetables (especially oranges, apples and carrots).

We have during our investigation and efforts to fractionally extract the most desirable constituents and leave out the less soluble and undesirable constituents by a very mild extraction, concentration and drying procedure as mentioned above succeeded in getting a superior product having a combination of ingredients described that have the unexpectedly superior property of several fold rapid intradermal transport of (1) Vitamin C derived from gallo-ellagi tannins and (2) hydrogen ions, especially on higher dilution of the extract, which is a property ideally suitable for skin applications using low doses of extract. Compositions having the extract of *Emblica officinalis* will be useful for all the skin applications of Vitamin C active compositions as described in other studies. One embodiment of the extract of *Emblica officinalis* is referred to as "C-COS™".

In one embodiment, a transdermal formulation having an extract of *Emblica officinalis* fruit exhibits about a 2 fold greater migration of Vitamin C (which includes reductones; and may include free Vitamin C and/or Vitamin C like molecules) across a skin surface, as compared to a transdermal formulation having Vitamin C (or ascorbic acid) without the extract. In one embodiment, a transdermal formulation having an extract of *Emblica officinalis* exhibits about a 2 fold to about a 7 fold greater migration of Vitamin C across a skin surface as compared to a transdermal formulation having Vitamin C without the extract. In one embodiment, a transdermal formulation having an of *Emblica officinalis* exhibits about a 2 fold to about a 5 fold greater migration of Vitamin C across a skin surface as compared to a transdermal formulation having Vitamin C without the extract. In one embodiment, a transdermal formulation having about 10 mg of the extract exhibits about a 2-fold greater migration of Vitamin C across guinea pig abdominal skin as compared to a transdermal formulation having about 10 mg of Vitamin C without the extract. In one embodiment, a transdermal formulation having about 10 mg of the extract exhibits about a 2-fold to about a 5 fold greater migration of Vitamin C across guinea pig abdominal skin as compared to a transdermal formulation having about 10 mg of Vitamin C without the extract. In one embodiment, a transdermal formulation having about 10 mg of the extract exhibits about a 2-fold to about a 5 fold greater migration of Vitamin C across guinea pig abdominal skin as compared to a transdermal formulation having about 10 mg of Vitamin C without the extract.

Another important discovery that has of been made during our investigations of the extract of *Emblica officinalis*, is that there is a several fold faster transfer of $H^+$ ions from the application of the extract of *Emblica officinalis* on the skin surface into the skin layers. The presence of active oxygen converts DOPA to DOPA-Quinone which is further converted to melanin which is dark brown and it further polymerizes to black melanin pigment which is responsible for black and brown skins. It has come to our observation during our investigations that the extract of *Emblica officinalis* transfers hydrogen ions across the membrane far faster than Vitamin C preparations do. Surprisingly we also discovered that the rate of transfer of these hydrogen ions was exponentially proportional to the dilution of the extract of *Emblica officinalis*. The results showed that the extract of *Emblica officinalis*, which was prepared by the disclosed mild process, was suitable as an agent for delivering greater amounts of Vitamin C and greater amount of hydrogen ions as compared to administration of Vitamin C (ascorbic acid) alone.

In one embodiment, a transdermal formulation having an extract of *Emblica officinalis* fruit exhibits about a 2 fold greater migration of $H^+$ ions across a skin surface as compared to a transdermal formulation having Vitamin C without the extract. In one embodiment, a transdermal formulation having an extract of *Emblica officinalis* fruit exhibits about a 2 fold to about a 13 fold greater migration of $H^+$ ions across a skin surface as compared to a transdermal formulation having Vitamin C without the extract. In one embodiment, a transdermal formulation having an extract of *Emblica officinalis* fruit exhibits about 2 fold to about a 10 fold greater migration of $H^+$ ions across a skin surface as compared to a transdermal formulation having Vitamin C without the extract. In one embodiment, a transdermal formulation having an extract of *Emblica officinalis* fruit exhibits about 2 fold to about 8 fold greater migration of $H^{30}$ ions across a skin surface as compared to a transdermal formulation having Vitamin C without the extract. In one embodiment, a transdermal formulation having an extract of *Emblica officinalis* fruit exhibits about 2 fold to about a 5 fold greater migration of $H^+$ ions across a skin surface as compared to a transdermal formulation having Vitamin C without the extract. In one embodiment, a transdermal formulation having an extract of *Emblica officinalis* fruit includes about 10 mg of the extract, and, the composition exhibits about a 2-fold greater migration of $H^+$ ions across guinea pig abdominal skin as compared to a transdermal formulation having about 10 mg of Vitamin C without the extract. In one embodiment, a transdermal formulation having an extract of *Emblica officinalis* fruit, which includes about 10 mg of the extract. The a transdermal formulation having the extract exhibits about a 2-fold greater migration of $H^+$ ions across guinea pig abdominal skin as compared to a transdermal formulation having an about 10 mg of Vitamin C without the extract. In one embodiment, a transdermal formulation having an extract of *Emblica officinalis* fruit includes about 10 mg of the extract, and, the composition exhibits about a 2-fold to about a 13 fold greater migration of $H^+$ ions across guinea pig abdominal skin as compared to a transdermal formulation having about 10 mg of Vitamin C without the extract. In one embodiment, a transdermal formulation having an extract of *Emblica officinalis* fruit includes about 10 mg of the extract, and, the transdermal formulation exhibits about a 2-fold to about a 10 fold greater migration of $H^+$ ions across guinea pig abdominal skin as compared to a transdermal formulation having about 10 mg of Vitamin C without the extract. In one embodiment, a transdermal formulation having an extract of *Emblica officinalis* fruit includes about 10 mg of the extract, and, the transdermal formulation exhibits about a 2-fold to about a 8 fold greater migration of $H^+$ ions across guinea pig abdominal skin as compared to a transdermal formulation having about 10 mg of Vitamin C without the extract. In one embodiment, a transdermal formulation having an extract of *Emblica officinalis* fruit includes about 10 mg of the extract, and, the composition exhibits about a 2-fold to about a 5 fold greater migration of $H^+$ ions across guinea pig abdominal skin as compared to a transdermal formulation having about 10 mg of Vitamin C without the extract.

A still more interesting phenomenon we observed is that the polyphenols become attached to the outer skin and behave as a protective agent against UV light. UV radiation is responsible for initiating the formation of melanin pigments and also free radicals. The formation of the UV protecting layer by the polyphenols protects the skin against UV light and its deleterious effects and discoloration of the skin and should cumulatively prevent melanoma, which is a form of cancer of the skin. We further discovered that not even a trace of the polyphenols crossed the skin in the in vitro study using guinea-pig-skin.

It is likely that the migration of the Vitamin C or molecules having Vitamin C like activity, or the reductone moiety of Vitamin C across the skin surface is closely associated with the binding of the polyphenol to the skin surface. Polyphenol might bind with the skin proteins providing protection against the passing of actinic (UV) light into the skin.

So it becomes evident that there is some relationship of the combining of the polyphenols with the outer surface of the skin and the faster release of the Vitamin C present in the less stable furanose (6-membered ring) structure, possibly changing over to the linear structure and crossing the epidermis of the skin and assuming its naturally stable pyranose (5-membered ring) structure and continuing with the normal antioxidant and inductive function for collagen synthesis.

With these results we have discovered an improved product, namely, an extract of *Emblica officinalis*, a method to prepare the same and properties of the extract of *Emblica officinalis* that are immensely superior to any existing skin application, in that the extract of *Emblica officinalis* provides a superior rate of transfer of Vitamin C and hydrogen ions across the skin, and thereby, provides protection against aging, acts as a free radical scavenger, as an inhibitor of melanin synthesis and as a protector against UV and possibly other forms of actinic radiation, and, from polluting agents like ozone.

Transdermal Transport Studies.

The diffusion studies were carried out across the guinea pig abdominal skin. The diffusion cell had an upper chamber and a lower chamber. The guinea pig abdominal skin was placed between the upper and lower chambers of the diffusion cell, thereby separating the 2 chambers. The test composition was introduced into the upper chamber. Migration of the components from the upper chamber to the lower chamber (which had liquid or buffer at body pH) through the guinea pig abdominal skin allowed comparative studies for extent of migration of the components from different test compositions.

A test substance, such as, the extract of *Emblica officinalis* or Vitamin C, was introduced in the upper chamber. The lower chamber had a fluid at a pH of the human body. After introducing the test material in the upper chamber, the diffusion was carried out for 3 hours. At intervals, the fluid in the lower chamber was tested for Vitamin C by titration method using 2,6-dichloroindophenol dye (as per method described in Example 1) for hydrogen ions by the acidimetric method (as described in Example 10). The content of Vitamin C or hydrogen ions in the lower chamber of the diffusion cell following administration of either the extract of *Emblica officinalis* or the administration of Vitamin C formed the basis for determining difference in the extent in the migration of Vitamin C or hydrogen ions across the skin surface.

The lower chamber of the diffusion cells were filled with 15 ml of phosphate buffer, pH 7, and the prepared guinea pig skins were fixed on each diffusion cell between the upper and lower chambers of the diffusion cell. The temperature of the diffusion cell was maintained at 37° C.

100 mg of the extract of *Emblica officinalis* in the form of a 1% w/w gel in water and 10 mg of the extract of *Emblica officinalis* in the form of a paste with 20 microlitres of water were applied to membranes in the upper chamber on different diffusion cells. The extract of *Emblica officinalis* had the following composition (extract was prepared as in Example 1):

Galloellagic tannins: 35.5%
Vitamin C: 8%
Corilagin: 0.75%
Carbohydrate: 29%
Soluble fibre: 24.55%
Ellagic acid: 1%
Gallic acid: 1.2%.

Similarly standard ascorbic acid (Vitamin C) preparations of exactly similar amounts (10 mg or 100 mg) were also applied to different skin membranes of in the upper chamber of different diffusion cells.

The diffusion across the skin membrane of active ingredients, that is, scorbutic reductones (that is Vitamin C actives substances including ascorbic acid) and hydrogen ions was carried out for three hours. The amount of Vitamin C transported across the skin at the end of 0, 1, 2 and 3 hours was determined by withdrawing an aliquot of 1 ml from each lower chamber of the diffusion cell and titration with dichlorophenolindophenol reagent (as per the method provided in Example 1).

The hydrogen ion concentration in the lower chamber of the diffusion cell was also determined in each case by titration of one ml against a standard alkali using a micro burette system at hourly intervals for three hours. The receptor cell solutions a end of three hours were also analyzed by HPTLC for identity of the species. The results for migration of Vitamin C or Vitamin C like molecules, which are referred to as reductone or reductone equivalent, across the skin membrane are shown in Table 1. The results for migration of H$^+$ ions across the skin membrane are shown in Table 2.

TABLE 1

| Product | Administration of extract of *Emblica officinalis* | | Administration of ascorbic acid | |
|---|---|---|---|---|
| Quantity mg, applied on guinea pig membrane | 100 | 10 | 100 | 10 |
| Reductone equivalent present in application (in upper chamber of diffusion cell) in mg | 6.67 | 0.667 | 100 | 10 |
| Reductones transported across the guinea pig membrane in mg | 0.163 | 0.15 | 8.4 | 0.3 |
| Fraction trans-dermal percent | 2.44% | 22.49% | 8.4% | 3.0% |

Table 1 shows that upon administration of the extract of *Emblica officinalis* paste having 10 mg of extract, the migration of the reductones of Vitamin-C-activity across the skin membrane was 22.49% after 3 hours, whereas, the gel with pure Vitamin C without the extract of *Emblica officinalis* showed only 3% migration on the input Vitamin C actives at administration of the lower dose of 10 mg. At the higher side of dosage of 100 mg of the extract of *Emblica officinalis*, the percentage of migration of Vitamin C across the skin membrane was 2.44%, whereas, administration of ascorbic acid showed greater migration of Vitamin C across the skin membrane of about 8.44%.

The lesser migration of Vitamin C through the skin upon administration of greater amount of the extract of *Emblica officinalis* appears probably due to a saturation effect, i.e., due to the reaction of the hydroxyl ion of polyphenol (phenolic portion) combining with the skin membrane proteins and forming a less penetrable layer for the reductones, whereas such a layer is absent in the case of administration of Vitamin C alone. This shielding observed with administration of greater amount of the extract of *Emblica officinalis* is a very beneficial attribute of the extract of *Emblica officinalis* in cutting off harmful actinic radiations and pollutants like ozone. Thus it becomes clear that the gallo-ellagi tannins of the extract of *Emblica officinalis* are more effective in allowing migration of Vitamin C when the extract of *Emblica officinalis* is present in lower concentration, whereas, at a lower concentration, pure Vitamin C was very poor in its transdermal delivery of Vitamin C across the skin surface which may be related to the poor stability of Vitamin C also.

TABLE 2

Hydrogen ion concentration in mg/100 ml in the receptor compartment (lower chamber) at the end of 3 hours

| Quantity of extract or ascorbic acid applied in the upper chamber | Concentration of hydrogen ions transferred across skin surface following administration of extract of *Emblica officinalis* (mg/100 ml) | Concentration of hydrogen ions transferred across skin surface following administration of ascorbic acid (mg/ml) |
|---|---|---|
| 100 mg | 0.123 | 0.480 |
| 10 mg | 0.617 | 0.0467 |

The migration of H$^+$ ions was far more with administration of the extract of *Emblica officinalis*. The migration of H$^+$ ions was greater at the higher dilution of the extract of *Emblica officinalis*, reaching about 0.617 at the 10 mg dose level of substance, whereas, the migration of H$^+$ ions in the case of ascorbic acid treatment at the same dose level of 10 mg of Vitamin C was only 0.0467. Therefore, migration of H$^+$ ions was 13 times greater upon administration of the extract of *Emblica officinalis* than upon administration of ascorbic acid on a weight to weight basis. Considering that only about 7% of the composition of the extract of *Emblica officinalis* were reductone in the extract of *Emblica officinalis*, the ratio of H$^+$ ion migration upon administration of the extract of *Emblica officinalis* to that of administration of Vitamin C alone becomes 13×100/7, which is 185 times greater migration of Vitamin C from the extract of *Emblica officinalis* as compared to that of ascorbic acid alone.

This difference in migration of H$^+$ ions upon administration of extract of *Emblica officinalis* versus administration of Vitamin C alone is probably due to the presence of a large number of hydroxyl groups that are present in the tannoid substances, including, galloellagic tannins, in the extract of

*Emblica officinalis*, which combine with the skin surface proteins resulting release of more of hydrogen ions and thereby migration of greater amount of hydrogen ions across the skin surface. At the higher dose of 100 mg of the extract of *Emblica officinalis*, the ratio of hydrogen ions migrated from the extract of *Emblica officinalis* was 25% of that of ascorbic acid at equal weights of application but this becomes about 3.66 times greater migration of $H^+$ ions upon administration of the extract of *Emblica officinalis* as compared to the migration of $H^+$ ions upon administration of ascorbic acid when the active concentration of reductone in the extract of *Emblica officinalis* versus the active reductone content of Vitamin C administration alone is taken into account.

The difference in behavior of hydrogen ions as compared to the migration of Vitamin C across the skin surface at lower concentration of the extract of *Emblica officinalis* as compared to the reductone (administration of Vitamin C alone) is expected as the size of the $H^+$ ions is small enough to pass through the layer of phenolics-protein complex formed on the skin. The advantage of such higher transport of the $H^+$ ions is the lowering of pH in the epidermis and consequent faster reduction of melanin pigments in the presence of reductones. This also gives a better clinical benefit of the extract of *Emblica officinalis* vis-à-vis ascorbic acid. That only at lower dose levels of the extract of *Emblica officinalis*, the hydrogen ions are profusely delivered is an advantage that the extract of *Emblica officinalis* provides in preventing the hydrogen ions from reaching toxic concentrations but providing the right environment for free radical scavenging by the Vitamin C active reductones.

The radical scavenging property of the extract of *Emblica officinalis* using the DPPH (diphenylpicryl-hydrazyl) method showed an inhibition of +6.99% on a 10 mg dose whereas an equal dose of ascorbic acid showed a −4.66% inhibition showing the sheer superiority of the extract of *Emblica officinalis* as a free radical scavenger. The reason for superiority of the extract of *Emblica officinalis* is probably related to the process of preparation of the extract of *Emblica officinalis* which is highly effective in preserving the activity of the components of the extract of *Emblica officinalis*.

We have developed effective compositions of extract of *Emblica officinalis* to be applied to the skin for the applications described above. The novelty of the extract of *Emblica officinalis* is that it avoids completely the usual solvents and skin modifying agents which are usually used in the preparations as detailed in the patents referred by us and in general by the industry. The only diluents used in some embodiments of the transdermal formulations having the extract of *Emblica officinalis* are, for example, glycerol and ethanol. In some embodiments, butylatedhydroxyaanisole is the only stabilizer and EDTA the only metal chelating agent used. In some embodiments, microbial stabilizers may be used in pure water compositions (without glycerol or alcohols).

Dosage forms of the transdermal formulation include lotion, cream, ointment or gel for application to skin.

The formulations for transdermal application described are designed to prevent any immunological shock to the skin and to provide treatment in its natural environment, which is not possible, by introducing significant chemical agents like tween-80 in quantities that will be sensed by the skin as foreign and create a response.

A process is provided for the isolation of an enriched gallo-ellagi tannin fraction with Vitamin C activity having properties much superior to application of Vitamin C itself on a skin membrane. The extract of *Emblica officinalis* showed highly enhanced properties of transdermal delivery of Vitamin C and Vitamin C like reductones and hydrogen ions across the epidermis (outer skin) to the dermis (inner layer of the skin) which overcomes the clinical difficulty of transporting water soluble Vitamin C across the skin membranes.

An extract of *Emblica officinalis* and a process for very rapid transport of vitamin C across the epidermis (outer skin) to the dermis (inner layer of the skin) for the more effective synthesis of and repair of the structural protein of the skin, collagen, to prevent aging, wrinkling and sagging is provided.

An extract of *Emblica officinalis* with capability to effect an exponentially rapid transfer of hydrogen ions with dilution to help prevent the oxidation dihydroxyphenylalanine (DOPA) to form the colored melanin pigment thereby providing a healthy and smooth skin through the skin is provided.

A mild process to manufacture a "near nil artifact" dry extract of the mature fruits of *Emblica officinalis* or the Indian gooseberry retaining the sensitive active ingredients, gallo-ellagitannins, vitamin C, corrilagin, carbohydrate and soluble fibre using low temperature extraction followed by low temperature concentration using a technologically superior process making use of an Agitated Thin Film evaporator (ATFE), and low temperature drying using an Agitated Thin Film drier (ATFD) at a temperature not exceeding 95-100° C. at any stage of operation and under vacuum of about 500-600 mm of mercury (Hg) and involving specific controls at every stage so that the process does not cause formation of artifacts due to heat or oxygen.

One embodiment provides a method of preparing an extract of *Emblica officinalis*. The method includes pulping fruits of *Emblica officinalis* in water at room temperature of about 27° C. to obtain a pulp. The pulp is dried at a temperature of about 95-100° C., and, under a vacuum of about 500-600 mm of mercury to obtain the extract of *Emblica officinalis*. The extract is substantially a dry extract. The moisture content of the extract is less than 5%.

A composition using an embodiment of the *Emblica officinalis* dry extract and natural excipients avoiding any skin-sensitizing synthetic chemicals (usually used in the art) and to fight the toxic influence of UV radiation and ozone pollutants by forming a protective coating of polyphenol on the outer skin membrane with no passing of these polyphenols across the skin even in traces resulting in a perfect, superior anti oxidant and actinic-light shield is provided.

A transdermal formulation to effectively preserve and transfer the active ingredients, such as Vitamin C and $H^+$ ions, wherein the transdermal formulation includes gallo-ellagi-tannins, Vitamin C, corrilagin, carbohydrate and soluble fibre is provided.

A transdermal formulation to effectively preserve and transfer the active ingredients, such as Vitamin C and $H^+$ ions, or aci-reductones or simply reductones having vitamin C bioactivity and Vitamin C, wherein the composition includes Vitamin C and hydrolysable gallic and ellagic tannins is provided.

A transdermal formulation to provide protection to the skin from free radicals and, super oxide ion by the rapid transfer of released Vitamin C actives from the galloellagitannins in the dry extract of *Emblica officinalis* at a far superior rate compared to the poor transport of Vitamin C transfer across the membrane observed upon administration of Vitamin C alone to the skin.

A method of preventing the formation dark skin pigments by interfering with the biosynthesis of melanin and even reversing the same by the rapid transfer of hydrogen ions along with vitamin C actives, thereby helping to provide a fairer skin, is provided.

It will be readily understood by the skilled artisan that numerous alterations may be made to the examples and instructions given herein. These and other object and features of present invention will be made apparent from the following examples. The following examples as described are not intended to be construed as limiting the scope of the present invention.

EXAMPLES

Example 1

Processing of mature *Emblica officinalis*, that is, the Indian gooseberry fruits to get a "near-nil artifact" extract of *Emblica officinalis* (one embodiment is also referred to as "C-COSTM").

Mature Indian gooseberries were obtained from dry regions of Southern India during the months of October to December. The mature Indian gooseberries (*Emblica officinalis*) had "No- GMO"—certification (i.e. not genetically modified organism). The fruits were washed with water to remove any external natural adherent and cooled to 5° C. and stored at that temperature till they were taken for extraction. Purified water in a proportion of 100% w/v was added and the *Emblica officinalis* fruits were pulped using a tapered screw expeller (Steel tech Engineering, India) at 29 rpm with 15 HP.

The fruit slurry (also referred to as pulp) so obtained from the pulping machine was then centrifuged at 10,000 rpm and the supernatant was purified by passing through resin column with strong $H^+$ ion exchange resin to obtain a clear permeate. Then the clear permeate was sent for concentration in an Agitated Thin Film Evaporator (ATFE, M/s Techno Force, Mumbai, India.) under the following conditions:
a) Jacket Temperature: 95-100° C.; b) vacuum: 500-600 mm mercury (Hg); and c) Agitator speed: 380 rpm, to obtain a concentrate. The concentrate was finally dried in an Agitated Thin Film Drier (ATFD, m/s Techno Force—Mumbai, India.) under the following conditions: a) Jacket temperature of 95-100° C., and b) vacuum of 500-600 mm mercury, to get a free flowing, hygroscopic product, namely, the extract of *Emblica officinalis*, having a light brown color with or without a greenish tinge. The analytical profile of the extract of *Emblica officinalis*, as per HPLC/HPTLC and chemical analysis of galloellagitannins, gallic acid, ellagic acid, Vitamin C, corrilagin, carbohydrate and soluble fiber, by the methods described below gave the following composition:

Galloellagic tannins: 35.5%
Vitamin C: 8%
Corilagin: 0.75%
Carbohydrate: 29%
Soluble fibre: 24.55%
Ellagic acid: 1%
Gallic acid: 1.2%.

The extract was substantially free of moisture. Moisture content was less than 5%.

Method for Estimation of Corilagin in the Extract of *Emblica officinalis*

Corilagin was estimated by high performance liquid chromatography (HPLC) on a C18 column (250×4.6 mm, Shimadzu Co., Japan.). The mobile phase, solvent A (0.05% ortho phosphoric acid in 1 mM $KH_2PO_4$) and solvent B (Acetonitrile) was used under linear gradient conditions with an eluent flow rate of 1.5 ml/min. Corilagin was detected at 266 nm.

Standard was prepared by weighing 2 mg of standard (corilagin) (Chromodex, United States) and dissolved in 10 ml methanol. Sample was prepared by weighing 50 mg of the dry *Emblica officinalis* extract (prepared as in Example 1) and was made up to 50 ml with methanol. Both the sample and standard were filtered separately through a 0.2 μm membrane filter before injection into the HPLC column. The injection volume was 20 μl. Corilagin was detected at 266 nm. By comparing the area of standard and sample, the percentage of corilagin present in the sample was quantified.

Method for Estimation of Soluble Fiber in the Dry Extract of *Emblica officinalis*

Fibre was estimated by a gravimetric method. Two grams of dry extract of *Emblica officinalis* (prepared as in Example 1) was weighed and transferred to a 500 ml conical flask. Then 200 ml of 1.25% sulphuric acid solution was added and the resulting solution was refluxed for two hours with occasional shaking. The solution was then cooled and filtered through a filter paper and the residual part was transferred to the same 500 ml conical flask. 200 ml of 1.25% sodium hydroxide solution was added to the residual part and the mixture refluxed for two hours with occasional shaking. The mixture was cooled and filtered through a preheated and weighed silica crucible. The silica crucible was placed along with the residue in oven at 100° C. for overnight. The silica crucible was then taken out, cooled and weighed. The weight difference of empty crucible and crucible with residue gave the percentage of soluble fibre present in the sample of dry extract of *Emblica officinalis*.

Method for Analysis of Carbohydrate

Carbohydrate was estimated by a spectrophotometric method using anthrone reagent as described in David T Plummer—An introduction to practical biochemistry: p-183. Standard was prepared by weighing 0.02 g of glucose, and made up *Emblica officinalis* to 100 ml with water. The sample was made up by taking 0.05 g of dry extract of in 50 ml water. Anthrone reagent was prepared by taking 0.2 g anthrone in 100 ml concentrated $H_2SO_4$.

0.1 ml of the test solution (sample & standard) was taken in a 10 ml stoppered test tube and the solution was made up to 1 ml with distilled water (0.1 ml of test solution and 0.9 ml of distilled water). The tubes were kept on ice. 0.4 ml of anthrone reagent was added to the above solution and mixed rapidly. The tubes were closed and placed in boiling water bath for 10 minutes. Absorbance was noted at 620 nm after cooling the solution. By comparing the absorbance and concentration of standard and sample, the percentage of carbohydrate can be calculated using the formula:

$$\frac{\text{Absorbance of sample} \times \text{Concentration of standard}}{\text{Absorbance of standard} \times \text{Concentration of sample}}$$

Method of Estimation of Vitamin C

Vitamin C was estimated by the method as provided in AOAC method (Association of Analytical chemists), Official Method of analysis (1984) p-844. 1 gm of sample (dry extract of *Emblica officinalis* as prepared in Example 1) was taken and made up to 100 ml with 3% $HPO_3$, filtered or centrifuged to obtain a supernatant. To an aliquot (5 ml) of supernatant of the $HPO_3$ extract 2.5 ml of acetone was added and the resulting solution was titrated with dye 2,6-dichloro indophenol until a faint pink color persisted for 15 seconds. The concentration of Vitamin C in the sample was expressed as mg ascorbic acid equivalent to 1 ml of the dye solution. From that vitamin C in 100 g of the extract of *Emblica officinalis* was calculated.

Method for Estimation of Free Ellazic Acid (Before Hydrolysis)

Ellagic acid was analyzed by HPLC method. (See, Navindra P. Seeram, R Lee and D Heber, "Bioavailability of ellagic acid in human plasma after consumption of ellagitannins from pomegranate juice "(2004)). Accurately weighed 10 mg standard of ellagic acid (Sigma, USA) was dissolved in 25 ml of methanol. The standard solution was filtered through a 0.2 μm membrane filter before injection. One gm of the sample (dry extract of *Emblica Officinalis*) was taken in a 100 ml standard flask and made up to the volume with methanol. 10 ml of the sample solution was further diluted to 50 ml with methanol, mixed well and filtered through a 0.2 μm membrane filter before injection (20 μinjection volume). Ellagic acid was estimated by HPLC on a C18 column (250×4.6 mm). Mobile phase, solvent A (2% Acetic acid in water) and solvent B ( 2% Aqueous Acetic acid in water) was used under linear gradient conditions with eluent flow rate of 1.0 ml/min. Ellagic acid was detected at 366 nm. By comparing the area of standard and sample, the percentage of Ellagic acid is quantified by the following formula:

$$\% \text{ of free ellagic acid} = \frac{\text{Concentration of standard} \times \text{Area of sample}}{\text{Area of standard Concentration of sample}}$$

Method for Estimation of Free Gallic Acid (Before Hydrolysis)

One gm of the sample (dry extract of *Emblica Officinalis*) was taken in a 100 ml standard flask and made up to 100 ml with methanol. 10 ml of the above solution was further diluted to 50 ml with methanol. Percentage of free gallic acid was determined by High Performance Thin Layer Chromatography (HPTLC) in a precoated silica gel plate of 0.2 mm thickness. About 10 mg of gallic Acid of 98% purity was weighed into a 100 ml volumetric flask and made up 100 ml with methanol is taken as the standard solution. The mobile phase used was benzene, methanol & glacial acetic acid ( 90:16:8). The amount of gallic acid in the sample extract of *Emblica officinalis* was calculated by:

$$\% \text{ of free gallic acid} = \frac{\text{Concentration of standard} \times \text{Area of sample}}{\text{Area of standard Concentration of sample}}.$$

Method of Estimation of Hydrolysable Gallo Ellagic Tannins

Hydrolysable galloellagic tannins were estimated by HPTLC (high performance thin layer chromatography) method using equipment from Desaga (Sarstedt—gruppe). About 1 gm of sample (dry extract of *Emblica Officinalis*) was weighed and transferred to a 100 ml round bottom flask fitted with a ground glass joint. 25 ml of distilled water and 3.75 ml of concentrated hydrochloric acid was added and the solution was refluxed for 3 hours in a heating mantle. The solution was cooled and made up to 100 ml with methanol in a 100 ml standard flask. 10 ml of above solution was diluted to 50 ml with methanol and percentage of hydrolysable gallo ellagic tannins was determined by High Performance Thin Layer Chromatography (HPTLC) in a precoated silica gel plate of 0.2 mm thickness. About 10 mg of gallic Acid of 98% purity was weighed into a 100 ml volumetric flask and made up 100 ml with methanol was taken as the standard solution. The mobile phase used was benzene, methanol & glacial acetic acid (90:16:8). The silica plate was derivatized with 1% alcoholic ferric chloride and dried for 10 minutes and then scanned at 570 nm. By comparing the area of standard and sample, the percentage of hydrolysable galloellagic tannins in the sample of dry extract of *Emblica Officinalis* was quantified by the following formula:

$$\% \text{ Hydrolysable gallo ellagic acid tannins} = \frac{\text{Concentration of standard}}{\text{Area of standard}} \times \frac{\text{Area of sample} \times 2}{\text{Concentration of sample}}$$

Method of Analysis of Polyphenols By Titration Method 50 mg of sample (dry extract of *Emblica Officinalis*) was accurately weighed and transferred into a 50 ml standard flask and made up to a 50 ml solution with methanol. 3 ml of the solution was transferred into a conical flask, 15 ml of methanol and 1 ml of indigo carmine solution were added, which was then titrated against a 0.04 N standardized $KMnO_4$ solution. The end point of the titration was determined by changing of the blue color of the solution to golden yellow. The volume of $KMnO_4$ at the titration end point was noted. The experiment was repeated till two concordant 1 values of the volume of $KMnO_4$ at the titration end point were obtained. A blank titration was done without taking the sample (having the dry extract of *Emblica Officinalis* prepared as in Example 1) solution. The titration was repeated with a standard (catechin, Sigma, USA). By measuring the purity of standard the amount of total polyphenol present in the sample (having the dry extract of *Emblica Officinalis* prepared as in Example 1) was calculated.

Example 2

In some batches of extract, the following composition of extract of *Emblica officinalis* was obtained following the procedure for extract preparation as outlined in Example 1:
Galloellagic tannins: 34%;
Vitamin C—7.6%;
Corilagin—2%;
Carbohydrate—32%, and
Soluble fibre—24.4%.
The methods used for detection of galloellagitannins, Vitamin C, corilagin, carbohydrate, soluble fiber, gallic acid and ellagic acid in the extract were as outlined in Example 1.

Example 3

Totally Herbal fairness composition
Ingredient parts of transdermal formulation by weight
*Emblica officinalis* extract (composition as provided in Example 2) 1.5;
Aloe Vera gel 10.0;
Glycerin 25.0;
Anise oil 0.5; and,
Water to 100.
Aloe Vera gel was diluted with 25 ml water to obtain a solution. Anise oil and glycerin were slowly stirred into the solution and homogenized to obtain a homogenate. A solution of *Emblica officinalis* extract (prepared as in Example 1) was prepared by dissolving 1.5 parts of the *Emblica officinalis* extract in 20 ml water. The solution having the *Emblica officinalis* extract (prepared as in Example 1) was added to the homogenate with homogenization and the final volume of the composition was made up to 100 ml.

Example 4

In some batches of extract, the following composition of extract of *Emblica officinalis* was obtained following the procedure for extract preparation as outlined in Example 1:
Galloellagic tannins: 35.5%;
Vitamin C: 7%;

Corilagin: 2.5%;
Carbohydrate: 33%; and,
Soluble fibre: 22%.

The methods used for detection of galloellagitannins, Vitamin C, corilagin, carbohydrate, soluble fiber, gallic acid and ellagic acid were also as outlined in Example 1.

Example 5

Totally herbal Fairness composition:
Ingredient of transdermal formulation in parts by weight
*Emblica officinalis* extract (composition as provided in Example 4) 1.0;
Water 25.0;
Ethanol 50.0;
Ascorbic acid 1.0;
Methyl paraben 0.25; and,
Neutralized with triethanolamine to pH 6.5 to 7.5.

Ascorbic acid, methylparaben and *Emblica officinalis* extract (prepared as in Example 1) were combined and dissolved in water to form a mixture. Ethanol was added to the mixture and pH of the resulting solution was adjusted to about 6.5-7.5 using triethanolamine. The ingredients listed for the composition provide a ratio of the *Emblica officinalis* extract (prepared as in Example 1) to the other components, namely, water, ethanol, ascorbic acid and methyl paraben.

Example 6

In one batch of extract of *Emblica officinalis* prepared as in Example 1, the carbohydrate content of the extract as estimated by spectrophotometric method was 34.9%. Soluble fibre estimated by gravimetrically was 24.5%.

Example 7

In one batch of extract of *Emblica officinalis* prepared as in Example 1, the carbohydrate content of the extract as estimated by spectrophotometric method was 17.4%. Soluble fibre estimated by gravimetrically was 13.1%.

Example 8

In one batch of extract of *Emblica officinalis* prepared as in Example 1, the carbohydrate content of the extract as estimated by spectrophotometric method was 22.5%. Soluble fibre estimated by gravimetrically was 17.4%.

Example 9

In one batch of extract of *Emblica officinalis* prepared as in Example 1, the carbohydrate content of the extract as estimated by spectrophotometric method was found to be 10.6%. Soluble fibre estimated by gravimetrically was about 7.8%.

Example 10

Acidimetric Analysis of $H^+$ Ion Concentration

About 10 g of the sample (dry extract of *Emblica officinalis* as prepared in Example 1 or an aliquot of the liquid from the lower chamber of the diffusion cell) was weighed and dissolved in 50 ml of a mixture of equal volumes of alcohol and ether (which were previously neutralized to phenolphthalein with 0.1 N sodium hydroxide). Added 1 ml of phenolphthalein to the test sample. The sample was titrated with 0.1 N sodium hydroxide. The end point of the titration was determined by the appearance of faint pink color. At the titration end point, the volume of 0.1 N sodium hydroxide, was noted. The experiment was repeated till two concordant values were obtained for the volume of 0.1 N sodium hydroxide at the titration end point. From the volume of sodium hydroxide used, the $H^+$ ion concentration was calculated using the formula:

$$H^+ \text{ion concentration} = \frac{n \times 56.1 \times \text{Normality of sodium hydroxide}}{W}$$

Where, n=Number of ml of 0.1 N sodium hydroxide required
W=Weight of sample in grams taken for analysis Changes in composition with different excipients can be made based on the art. Amount of extract of *Emblica officinalis* in transdermal formulations may also be altered depending upon clinical need of the active ingredient.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A method of increasing transfer of Vitamin C across a skin surface of a subject in need thereof, the method comprising, administering a transdermal formulation comprising an extract *Emblica officinalis* fruit,
   wherein the extract of *Emblica officinalis* fruit comprises, by weight,
   about 35±5% of galloellagitannin;
   about 1-9% of Vitamin C; and,
   about 5-60 of carbohydrate,
   wherein about 0.5-5% of the galloellagitannin is comprised of corilagin,
   wherein about 2-25 % of the carbohydrate is comprised of soluble fiber, and
   wherein the extract of *Emblica officinalis* fruit is prepared by a process comprising:
   pulping fruits of *Emblica officinalis* in water to obtain a slurry,
   centrifuging the slurry to obtain a supernatant,
   passing the supernatant through a strong $H^+$ ion exchange resin to obtain a permeate, wherein the permeate is said extract of *Emblica officinalis*.

2. A method of increasing transfer of $H^+$ ion across a skin surface of a subject in need thereof, the method comprising, administering a transdermal formulation comprising an extract of *Emblica officinalis* fruit, wherein the extract of *Emblica officinalis* fruit comprises, by weight,
   about 35±5% of galloellagitannin;
   about 1-9% of Vitamin C; and,
   about 5-60% of carbohydrate,
   wherein about 0.5-5% of the galloellgitannin is comprised of corilagin,
   wherein about 2-25% of the carbohydrate is comprised of soluble fiber, and
   wherein the extract of *Emblica officinalis* fruit is prepared by a process comprising;
   pulping fruits of *Emblica officinalis* in water to obtain a slurry,
   centrifuging the slurry to obtain a supernatant,
   passing the supernatant through a strong $H^+$ ion exchange resin to obtain a permeate, wherein the permeate is said extract of *Emblica officinalis*.

3. A method of increasing transfer of Vitamin C across a skin surface of a subject in need thereof, the method comprising administering a transdermal formulation comprising an extract of *Emblica officinalis* fruit wherein the extract of *Emblica officinalis* fruit comprises, by weight,
- about 35-50% polyphenol, and wherein about 0.5-5% of the polyphenol is comprised of corilagin, and
- wherein the extract of *Emblica officinalis* fruit is prepared by a process comprising;
- pulping fruits of *Emblica officinalis* in water to obtain a slurry,
- centrifuging the slurry to obtain a supernatant,
- passing the supernatant through a strong $H^+$ ion exchange resin to obtain a permeate, wherein the permeate is said extract of *Emblica officinalis*.

4. A method of increasing transfer of $H^+$ ion across a skin surface of a subject in need thereof, the method comprising administering a transdermal formulation comprising an extract of *Emblica officinalis* fruit,
- wherein the extract of *Emblica officinalis* fruit comprises, by weight,
- about 35-50% and wherein about 0.5-5% of the polyphenol is comprised of corilagin, and
- wherein the extract of *Emblica officinalis* fruit is prepared by a process comprising:
- pulping fruits of *Emblica officinalis* in water to obtain a slurry,
- centrifuging the slurry to obtain a supernatant,
- passing the supernatant through a strong $H^+$ ion exchange resin to obtain a permeate, wherein the permeate is said extract of *Emblica officinalis*.

* * * * *